United States Patent [19]

Merten et al.

[11] 4,089,860
[45] May 16, 1978

[54] PREPARATION OF HYDANTOINS BY REACTING ESTERS OF ETHYLENE-1,2-DICARBOXYLIC ACIDS AND UREAS AND THIOUREAS

[75] Inventors: Rudolf Merten; Ludwig Rottmaier, both of Leverkusen, Germany

[73] Assignee: Bayer Aktiengesellschaft, Germany

[21] Appl. No.: 719,248

[22] Filed: Aug. 31, 1976

[30] Foreign Application Priority Data

Sep. 6, 1975 Germany .............................. 2539730

[51] Int. Cl.² .................. C07D 233/78; C07D 233/80
[52] U.S. Cl. .............................. 544/295; 260/77.5 R; 544/357; 544/295; 544/296; 544/364; 544/370; 544/322; 260/294.8 D; 260/294.8 E; 260/294.8 H; 260/295 E; 260/295 PA; 260/295 E; 260/295 PA; 260/295.5 D; 548/309; 548/310; 548/313

[58] Field of Search ........ 260/309.5, 77.5 R, 256.4 R, 260/256.4 N, 268 H, 268 N, 268 PL, 268 FT, 294.8 E, 294.8 H, 294.8 D, 295 E, 295 PA, 256.5 R, 295.5 D; 548/313, 310, 309

[56] References Cited

U.S. PATENT DOCUMENTS

| 2,895,817 | 7/1959 | Luckenbauch ................... 260/309.5 |
| 3,818,032 | 6/1974 | Moser et al. ...................... 260/309.5 |

OTHER PUBLICATIONS

Ware Chem. Reviews 1950, vol. 46, p. 416.

*Primary Examiner*—Natalie Trousof
*Attorney, Agent, or Firm*—Connolly and Hutz

[57] ABSTRACT

A process for the preparation of (thio) hydantoins modified with carboxylic ester groups, wherein 1,2-ethylene dicarbocylic acid esters which may be substituted are reacted with (thio) urea compounds in a single stage reaction.

6 Claims, No Drawings

PREPARATION OF HYDANTOINS BY REACTING ESTERS OF ETHYLENE-1,2-DICARBOXYLIC ACIDS AND UREAS AND THIOUREAS

This invention relates to a process for the preparation of modified compounds which contain, in the molecule, at least one hydantoin or thiohdantoin ring substituted with carboxylic acid ester groups. These compounds correspond to the general formula (I)

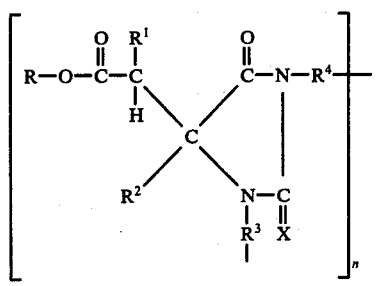

(I)

in which R represents an alkyl group; $R^1$ and $R^2$ represent hydrogen or an alkyl group which may be substituted; $R^3$ represents hydrogen; an alkyl or cycloalkyl group which both may be substituted with halogen, hydroxyl or alkoxy; an aryl group which may be substituted with nitro, halogen, alkyl, alkoxy, haloalkyl or hydroxyl; an aralkyl group or a heterocyclic group; $R^4$ represents hydrogen; an alkyl or a cycloalkyl group which both may be substituted with halogen, hydroxyl or alkoxy; an aryl group which may be substituted with nitro, halogen, alkyl, alkoxy, haloalkyl and/or hydroxyl; an aralkyl group or a heterocyclic group; X represents oxygen or sulphur and n represents an integer of from 1 to 30, preferably 1 or 2.

Groups $R^3$ and $R^4$ may be polyfunctional and are preferably difunctional. Products having the recurrent formula (I) wherein $n > 1$ are obtained in this way.

The groups $R^1$ and $R^2$ may, in particular, represent hydrogen or R, $R^1$ or $R^2$ may represent $C_1$ to $C_{18}$ alkyl groups and $R^3$ may represent hydrogen or $C_1$ to $C_{18}$ alkyl groups or aryl groups with $C_6$ to $C_{16}$ such as phenyl, naphthyl, bisphenyl, diphenylether, benzyl groups or heterocyclic groups. $R^4$ may have the meaning of groups $R^3$ with a valency of between 1 and 3 according to the size of n.

Heterocyclic groups are preferably 5- or 6-membered rings containing one or more oxygen, nitrogen and/or sulphur atoms, e.g. groups derived from furan, pyridine, thiophene, imidazole, pyrimidine or piperazine.

The preparation of compounds of the general formula (I) has already been described before and could be carried out, for example, by reacting aspartic acid ester, which may be formed in situ from 1,2-ethylene-dicarboxylic acid esters and amines with isocyanates and isothiocyanates followed by thermal or catalytic ring closure. This process proceeds via several stages.

It has now surprisingly been found that hydantoin compounds modified with carboxylic acid ester groups can be obtained directly by a single stage reaction with very high yields when ureas are reacted with 1,2-ethylene-dicarboxylic acid esters which may be substituted.

The present invention therefore relates to a process for the preparation of (thio) hydantoins modified with carboxylic ester groups, wherein 1,2-ethylene dicarbocylic acid esters which may be substituted are reacted with (thio) urea compounds in a single stage reaction.

Apart from being only a single reaction, the process according to the invention has the advantage of avoiding side reactions by using less basic starting components.

The process according to the invention may be represented by the following equation in which the general groups have the meaning indicated above.

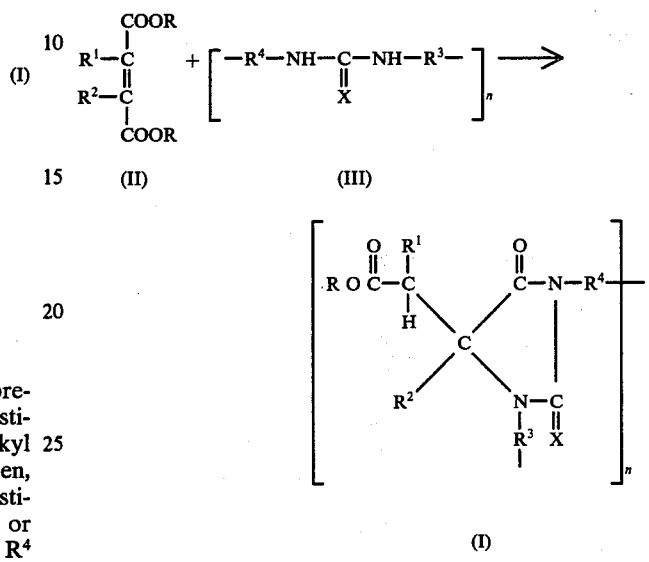

The esters of ethylene-1,2-dicarboxylic acids (Formula II) used in the reaction are preferably $C_1$–$C_{20}$alkyl di-esters of maleic acid such as dimethyl, diethyl or dibutyl maleate and the corresponding esters of fumaric acid. The previously prepared esters may be introduced into the process, but, if desired, they may be prepared in situ from the corresponding alcohol (in excess) and maleic acid anhydride, particularly since an excess of alcohol does not interfere with the subsequent addition reaction with the ureas or thioureas. The process may, of course, also be carried out with other maleic acid esters using polyhydric alcohols such as glycol, glycerol or trimethylolpropane. These esters can easily be prepared in a previous operation from the corresponding glycol and maleic acid anhydride. Moreover, instead of esters of maleic acid, suitable substituted maleic acids may be used, especially $C_1$–$C_{20}$alkyl substituted maleic acids such as methyl, dimethyl, ethyl or butyl maleic acid. The corresponding fumaric acid esters may also be used in all these cases.

The mono- or polyureas or thioureas of the general formula III used in the reaction according to the invention are generally known. In this formula, $R^4$ and $R^3$, which may be the same or different, are preferably derived from hydrogen, $C_2$–$C_{20}$ aliphatic hydrocarbons such as ethane, propane, butane, hexane, stearine, cyclohexane, $C_6$–$C_{16}$ aromatics such as benzene, toluene, xylene, methoxybenzene, chlorobenzene, benzidine, diphenyl, diphenylether, diphenylmethane, diphenylsulphone or naphthalene.

The reaction between 1,2-ethylene-dicarboxylic acid esters and ureas is generally carried out at temperatures of from 80° to 250° C, preferably 150° to 200° C, optionally in inert solvents.

The inert solvents used are preferably aliphatic or aromatic hydrocarbons and their halogenation products, e.g. diisopropylbenzene, methylnaphthalene or di- or tri-chlorobenzene, or polar solvents such as N- methylpyrrolidone, dimethylformamide, diethylacetamide, phenol, cresols or xylenols.

Reaction times of from 1 to 10 hours are generally required. The addition and cyclisation reactions may be carried out with heating. To ensure a smoother reaction, it is frequently advantageous to add a catalyst, especially one which is acid in reaction. When acid solvents are used, e.g. phenols or cresols, the acidity of these solvents is sufficient to ensure a sufficiently short reaction time. In other cases, acids may be added, for example carboxylic acids with $C_2$ to $C_{10}$ such as acetic acid, butyric acid, pivalic acid, benzoic acid or trichloroacetic, or p-toluenesulphonic acid or phenols which have been acidified by electrophilic substitution.

The reaction is generally carried out using stoichiometric quantities although one of the components may be used in excess, for example to serve as solvent. The reaction products obtained, some of which are already known, can be processed by the usual methods, for example by the distillation or crystallisation processes described in the examples given later.

The hydantoins modified with ester groups obtained according to the invention may be converted in the usual manner into other derivatives of the acid from which they are derived, for example they may be hydrolysed to the free acids or they may be converted into amides by reaction with primary or secondary amines or they may be transesterified with other monohydric or polyhydric alcohols.

They may be used in particular for the production of synthetic resins and particularly of synthetic resins with elevated temperature resistance and high elasticity. The inventive monofunctional or polyfunctional esters or acids are resistant to temperatures above 300° C without decomposition and can be built into linear or branched synthetic resins in the usual manner or as monofunctional compounds they may be present as end groups or side groups thus functioning as antistatic or lubricant agent. If, desired, this conversion into polymeric components may be carried out subsequent to preparation of the acids.

This formation of polymers is generally carried out by reaction of the ester groups with polyhydric alcohols or polyvalent functional amines to produce polyesters or polyamides. The polymers obtained therefore contain ester or amide groups in addition to the (thio) hydantoin rings. Furthermore, the polymers may also be converted by known methods into polymers which in addition contain groups such as imidazole, benzimidazole, benzimide or pyromellitic acid imide rings.

Polymers which have been modified with hydantoins prepared according to the invention are found to have improved temperature resistance and can be used for the preparation of lacquers.

EXAMPLE 1

Preparation of 1,3-dimethyl-5-(methoxycarbonyl-methylene)-hydantoin:

44 g of N,N'-dimethylurea were dissolved in 150 g of o-dichlorobenzene and reacted with 72 g of dimethylmaleate for 2 hours at 180°–185° C after the addition of 25 g of cresol. The solvent was removed from this reaction mixture and the residue was fractionated under vacuum, 85 g (= 85% of the theory) of the desired product distilling over at 0.07 Torr and 128° C. A purified product melting at 49.5° C could be obtained by dissolving the crude product in chloroform and reprecipitating it with ether. The structure of the purified product was confirmed by IR and NMR spectra and by elementary analysis.

Calculated: C = 48 % H = 6 % N = 14 %: Found: C = 47.8% H = 5.8% N = 13.8%.

EXAMPLE 2

Preparation of 5-(methoxycarbonyl-methylene)-hydantoin:

60 g of urea were dissolved in 500 g of cresol and then slowly heated to 170° C together with 144 g of dimethyl maleate. A sublimate of fumaric ester was obtained in the condenser. The reaction was stopped when only 12 g of methanol had distilled off. After removal of the solvent by evaporation under vacuum, unreacted urea was removed from the residue with dioxane. After removal of the dioxane, the residue was taken up in chloroform and shaken with water. When the aqueous phase was concentrated by evaporation, the desired product crystallised with a melting point of from 78° to 79° C. Its structure was confirmed by IR and NMR spectra and by elementary analysis.

(a) Calculated: C = 41.8% H = 4.6% N = 16.3% %: Found: C = 41.9% H = 4.6% N = 15.8%.

An addition product of hydantoin and dimethylmaleate represented by the following structural formula could be isolated from the chloroform phase:

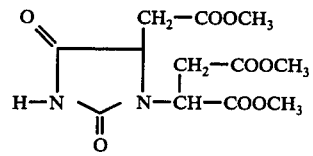

(b) Calculated: C = 45.6% H = 5.1% N = 8.9%: Found: C = 45.5% H = 5.0% N = 8.8%.

EXAMPLE 3

Preparation of 1-methyl[benzyl]-3-benzyl[methyl]-5-(methoxy-carbonyl-methylene)-hydantoin:

82 of N-methyl-N'-benzyl urea were dissolved in 230 g of cresol and 72 g of dimethylmaleate were added. After the reaction had continued for 1½ hours at 200° C, during which 13 g of methanol were liberated, the cresol had to be distilled off. After fractional distillation, a viscous liquid with a boiling point of 193° C/0.25 Torr was obtained as the main fraction. According to gas chromatographic analysis, it consisted of an isomeric mixture of about 80% of 1-methyl-3-benzyl-hydantoin and about 20% of 1-benzyl-3-methyl-hydantoin.

Calculated: C = 60.7% H =6.1% N = 10.1%: Found: C = 61.3% H = 6.2% N = %. 10.1%

EXAMPLE 4

Preparation of 1-methyl[cyclohexyl]-3-cyclohexyl[-methyl]-5-(methoxy-carbonyl-methylene)-hydantoin:

78 g of N-methyl-N'-cyclohexyl urea, 220 g of cresol and 72 g of dimethyl maleate were stirred at 185° C for one hour and then at 200° C for one hour. 15 g of methanol distilled over during this time. After fractional distillation, a main fraction boiling at 180°–185° C/0.08 Torr could be isolated. It consisted of an isomeric mixture of 1-methyl-3-cyclohexyl-hydantoin and 1-cyclohexyl-3-methylhydantoin but its exact composition could not be determined by gas chromatography.

Calculated: C = 58.2% H = 7.5% N = 10.4%: Found: C = 57.7% H = 7.8% N = 9.8%.

EXAMPLE 5

Preparation of 1-benzyl-3-phenyl-5-(methoxycarbonylmethylene)-hydantoin:

113 g of N-phenyl-N'-benzyl-urea were dissolved in 1000 g of o-dichlorobenzene; the solution was made acid with 2-ethyl-hexanoic acid and reacted with 72 g of dimethyl maleate. After a reaction time of 6 hours at 175° C, the solvent was distilled off and the residue triturated with ether. The product separated by suction filtration can be obtained pure by recrystallisation from toluene. The white crystals obtained have a melting point of 130° C and their structure was demonstrated by the IR and NMR spectra and elementary analysis.

Calculated: C = 67.4% H = 5.3% N = 8.3%:
Found: C = 67.3% H = 4.8% N = 8.1%.

EXAMPLE 6

Preparation of 1-methyl-3-phenyl-5-(methoxycarbonylmethylene)-hydantoin:

150 g of N-methyl-N'-phenyl urea were reacted with 144 g of dimethyl maleate in 450 g of phenol at 190° C. 25 g of methanol distilled over a period of 2 hours. Fractional distillation yielded a main fraction 182° C (0.14 mm Hg). When this fraction was dissolved in chloroform and then precipitated with ether in the cold, it yielded 114 g (=43.5% of the theory) of pure hydantoin, m.p. = 82° C. Its structure could be confirmed by elementary analysis and by the IR and NMR spectra.

Calculated: C = 59.5% H = 5.3% N = 10.7%:
Found: C = 59.6% H = 5.3% N = 11.0%.

EXAMPLE 7

Preparation of 1-methyl-5-(methoxycarbonylmethylene)-hydantoin:

Proceeding in a similar manner to Example 3, 222 g of methyl urea were dissolved in 1000 g of cresol, and 432 g of dimethylmaleate were added. After termination of the reaction during which 92 g of methanol were liberated, and after gas chromatographic analysis showed 95% conversion of the reactants, the cresol was distilled off and the residue fractionated under vacuum. The main fraction distilling over at 140° to 143° C/0.06 Torr was recrystallised from ethyl acetate. The identity of the pure substance obtained, which melted at 100° C, could be confirmed by the IR and NMR spectra and elementary analysis.

Calculated: C = 45.2% H = 5.4% N = 15.1%:
Found: C = 45.5% H = 5.6% N = 15.3%.

EXAMPLE 8 – 20

The ureas shown in the following Table were reacted with maleic acid esters in a similar manner to Example 7 and recrystallised after evaporation of the solvent.

| Example | Urea | maleic acid ester | Reaction temperature | Reaction time | Recrystallised from | Properties of product |
| --- | --- | --- | --- | --- | --- | --- |
| 8 | Phenyl urea | -dimethyl | 200° C | 2 h | Ethyl acetate | m.p. = 160° C |
| 9 | N-phenyl-N'-cyclo-hexyl-urea | dimethyl | 180 – 200° C | 2 h | ethanol/ether/petroleum ether | m.p. = 98° C |
| 10 | N,N'-distearyl-urea | dimethyl | 200° C | 2 h | ethanol | m.p. = 59° C |
| 11 | N,N'-dimethyl-urea | dibutyl | 200° C | 2 h | — | b.p.$_{0.06}$ = 129–130° C  n$_D^{20}$ = 1.4757 |
| 12 | Phenyl urea | di-sec.- | 180 – 200° C | 2 h | ethyl acetate | m.p. = 105° C |
| 13 | N,N'-dimethyl-thiourea | dimethyl | 180 – 200° C | 4 h | ether | m.p. = 78 – 79° C |
| 14 | N,N'-diphenyl-thiourea | dimethyl | 170 – 180° C | 2 h | ethyl acetate | m.p. = 126° C |
| 15 | N-phenyl-N'-butyl urea | diocta-decyl | 200° C | 2 h | cleaning petrol | m.p. = 58° C |
| 16 | N-methyl-N'-(3,4-dichloro-phenyl)-urea | dimethyl | 200° C | 1 h | purified over silica gel | n$_D^{20}$ = 1.5491 |
| 17 | N-methyl-N'-(2-methyl-phenyl)-urea | dimethyl | 180 – 200° C | 2 h | carbon tetra-chloride/ligroin | m.p. = 73° C |
| 18 | N-methyl-N'-(2-chlo-rophenyl)-urea | dimethyl | 200° C | 2 h | | b.p.$_{0.1}$ = 185 – 190° C |
| 19 | N-methyl-N'-(4-methoxyphenyl)-urea | dimethyl | 200° C | 2 h | ethyl acetate/ether | m.p. = 76 – 77° C |
| 20 | N-methyl-N'-naphthyl urea | dimethyl | 200° C | 2 h | ethyl acetate/petroleum ether | m.p. = 63° C |

TABLE 2

| Example | Theoretical analytical values | | | | | Found analytical values | | | | |
| --- | --- | --- | --- | --- | --- | --- | --- | --- | --- | --- |
| 8 | C = 58.2% | H = 4.8% | N = 11.3% | | | C = 58.4% | H = 4.9% | N = 11.3% | | |
| 9 | C = 65.5% | H = 6.6% | N = 8.5% | | | C = 65.4% | H = 6.8% | N = 8.6% | | |
| 10 | C = 74.5% | H = 11.8% | N = 4.1% | | | C = 74.9% | H = 11.8% | N = 3.9% | | |
| 11 | C = 54.6% | H = 7.5% | N = 11.6% | | | C = 54.8% | H = 7.7% | N = 11.7% | | |
| 12 | C = 62.1% | H = 6.2% | N = 9.6% | | | C = 61.8% | H = 6.5% | N = 9.7% | | |
| 13 | C = 44.5% | H = 5.6% | N = 13.0% | S = | 14.8% | C = 44.3% | H = 5.4% | N = 13.2% | S = | 15.0% |
| 14 | C < 63.5% | H = 4.7% | N = 8.2% | S = | 9.4% | C = 63.8% | H = 4.8% | N = 8.7% | S = | 9.3% |
| 15 | C = 73.2% | H = 10.0% | N = 5.2% | | | C = 73.0% | H = 9.8% | N = 5.2% | | |
| 16 | C = 47.2% | H = 3.7% | N = 8.5% | Cl = | 21.4% | C = 47.6% | H = 3.8% | N = 8.4% | Cl = | 21.3% |
| 17 | C = 60.9% | H = 5.8% | N = 10.2% | | | C = 60.6% | H = 5.7% | N = 10.3% | | |
| 18 | C = 52.6% | H = 4.4% | N = 9.4% | Cl = | 12.0% | C = 52.1% | H = 4.4% | N = 9.0% | Cl = | 12.1% |
| 19 | C = 57.5% | H = 5.5% | N = 9.6% | | | C = 57.7% | H = 5.4% | N = 9.7% | | |

| Example | Theoretical analytical values | Found analytical values |
|---|---|---|
| 20 | C = 65.3% H = 5.1% N = 9.0% | C = 65.5% H = 5.3% N = 8.9% |

EXAMPLE 21

Preparation of 4,4'-bis[3-methyl-5-(methoxycarbonylmethylene)-hydantoin-1]-diphenylmethane: 78 g of the urea

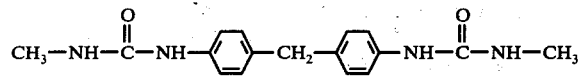

were dissolved in 600 g of cresol and reacted with 72 g of dimethylmaleate. When this mixture had been stirred for 2 hours at 200° C, the cresol had to be distilled off under vacuum. The residue was dissolved in ethyl acetate and precipitated with ether/ligroin. The resulting precipitate was found to have a melting point of 109° C and its identity could be confirmed by IR and NMR spectra and by elementary analysis:

Calculated: C = 60.4% H = 5.3% N = 10.4%:
Found: C = 60.5% H = 5.2% N = 10.2%.

EXAMPLE 22

Preparation of 1,5-dimethyl-3-phenyl-5-(methoxycarbonylmethylene)-hydantoin:

31.6 g of methyl maleic acid dimethyl ester and 30 g of N-methyl-N'-phenylurea were stirred in 50 g of phenol for 3 hours at 180° C. The reaction product was sufficiently concentrated by distilling off the solvent that the residue could be recrystallised from ethyl acetate. The resulting white crystals, whose structure was confirmed by IR and NMR spectra and elementary analysis, melt at 108° C.

Calculated: C = 60.8% H = 5.8% N = 10.1%:
Found: C = 60.6% H = 5.7% N = 10.0%.

EXAMPLE 23

Preparation of 1,5-dimethyl-5-(methoxycarbonylmethylene)-hydantoin: 63.2 g of citraconic acid dimethyl ester were dissolved in 100 g of o-dichlorobenzene. 29.6 g of methyl urea were added and the reaction mixture was adjusted to pH 4 with p-toluenesulphonic acid. After a reaction time of 3 hours at about 180° C, the solvent was distilled off and the residue fractionated. The fraction distilling over at 168°–172° C/0.15 Torr could be obtained in the pure form with an m.p. of 145° C by recrystallisation from ethyl acetate. The presumed structure of the product was confirmed by IR and NMR spectra and elementary analysis.

Calculated: C = 48 % H = 6 % N = 14 %: Found: C = 47.8% H = 5.9% N = 14.2%.

EXAMPLE 24

Preparation of 5-methyl-5-(methoxycarbonylmethylene)-hydantoin:

31.4 g of citraconic acid dimethyl ester and 12 g of urea were stirred in 50 g of cresol for 3 hours at 200° C. After fractional distillation, the main fraction (b.p. $_{0.2}$ 201°–205° C) was recrystallised from ethyl acetate. The pure substance was found to have a melting point of 148° C. This substance was identified by the IR and NMR spectra and elementary analysis:

Calculated: C = 45.2% H = 5.4% N = 15.0%:
Found: C = 45.5% H = 5.6% N = 14.9%.

EXAMPLE 25

Preparation of 1,5-dimethyl-3-phenyl-5-(n-butoxycarbonyl-methylene)-hydantoin 48.4 g of citraconic acid dibutyl ester were reacted with 30 g of N-methyl-N'-phenyl urea in 50 g of cresol. After fractional distillation, the major fraction (b.p.$_{0.1}$ = 180°–186° C) was recrystallised from cleaning petrol. The substance obtained, which had a melting point of 73° C, was found to have the expected structure as confirmed by elementary analysis and IR and NMR spectra.

Calculated: C = 64.2% H = 6.9% N = 8.8% Found: C = 64.4% H = 7.0% N = 8.6%

EXAMPLE 26

Preparation of 5-methyl-3-phenyl-5-(methoxycarbonylmethylene)-hydantoin 158 g of citraconic acid dimethyl ester and 161 g of phenyl urea were reacted together in 250 g of cresol at 180° C for 3 hours. The solvent was distilled off and the residue free from polar impurities by passage through a frit. A pure substance melting at 101° C could be obtained by recrystallisation from ethyl acetate. Its presumed structure was confirmed by elementary analysis and IR and NMR spectra.

Calculated: C = 59.6% H = 5.3% N = 10.7%
Found: C = 59.8% H = 5.2% N = 10.8%

EXAMPLE 27

Preparation of a polyhydantoin (a) 58 g of hexamethylene diamine were dissolved in 800 ml of toluene, and a solution of 125 g of diphenylmethane-4,4'-diisocyanate in 100 ml of toluene was added. The resulting precipitate of polyurea was suction filtered and dried in a vacuum drying cupboard at 60° C.

(b) 36.6 g of the polyurea prepared according to Example 27 (a) were suspended in 140 g of m-cresol. 28.8 g of dimethyl maleate were added and the mixture was stirred at 200° C for 6 hours. 200 g of a polyhydantoin solution which had a viscosity of 317cP$_{25}$ after dilution with an equal quantity of m-cresol was obtained. The solution can be used as electroinsulating lacquer which has a high temperature resistance and good elasticity. The IR spectrum was found to have the typical bands for this compound at 1720 cm$^{-1}$ and 1770 cm$^{-1}$.

What we claim is:

1. A process for preparing a compound of the formula

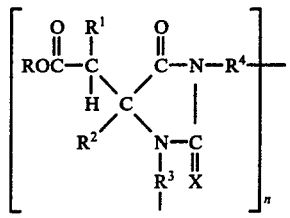

wherein R is alkyl having one to eighteen carbon atoms; $R^1$ and $R^2$ are hydrogen or alkyl having 1 to 18 carbon atoms; $R^3$ is monofunctional or polyfunctional and is selected from the group consisting of hydrogen; alkyl and cycloalkyl each having up to 18 carbon atoms; said alkyl and cycloalkyl substituted with halogen or hydroxy; aryl and aralkyl each having up to 16 carbon atoms; said aryl substituted with nitro, halogen, lower alkyl, lower alkoxy, or hydroxy; furan; pyridine; thiophene; imidazole; pyrimidine and piperazine; $R^4$ is monofunctional or polyfunctional and is selected from the group consisting of hydrogen; alkyl and cycloalkyl each having up to eighteen carbon atoms; said alkyl and said cycloalkyl substituted by halogen or hydroxy; aryl and aralkyl each having up to 16 carbon atoms; said aryl substituted with nitro, halogen, lower alkyl, lower alkoxy or hydroxy; furan; pyridine; thiophene; imidazole; pyrimidine and piperazine; X is O or S and $n$ is from 1 to 30, said process comprising reacting a compound of the formula

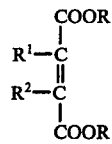

with a compound of the formula

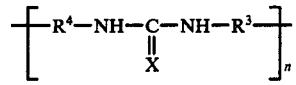

at a temperature of from 80° to 250° C in a single-stage reaction.

2. A process as claimed in claim 1 wherein $n$ represents 1 or 2.

3. A process as claimed in claim 1 wherein $R^3$ and/or $R^4$ is a difunctional group.

4. A process as claimed in claim 1 wherein the reaction is carried out at a temperature of from 150° to 200° C.

5. A process as claimed in claim 1 wherein the reaction is carried out in an inert solvent.

6. A process as claimed in claim 5 wherein the inert solvent is an aliphatic or aromatic hydrocarbon which may be halogenated or a polar solvent.

* * * * *